(12) United States Patent
Kim

(10) Patent No.: US 9,060,739 B2
(45) Date of Patent: Jun. 23, 2015

(54) PHOTOGRAPHING DEVICE INCLUDING A POWER TRANSMISSION BODY SELECTIVELY COUPLED TO A ROTATING ARM AND TO A SUPPORT

(75) Inventor: Jae-Hong Kim, Seoul (KR)

(73) Assignee: Rayence Co., Ltd., Gyeonggi-do (KR)

( * ) Notice: Subject to any disclaimer, the term of this patent is extended or adjusted under 35 U.S.C. 154(b) by 105 days.

(21) Appl. No.: 13/982,315

(22) PCT Filed: Mar. 31, 2011

(86) PCT No.: PCT/KR2011/002248
§ 371 (c)(1),
(2), (4) Date: Jul. 29, 2013

(87) PCT Pub. No.: WO2012/102435
PCT Pub. Date: Aug. 2, 2012

(65) Prior Publication Data
US 2013/0301796 A1  Nov. 14, 2013

(30) Foreign Application Priority Data

Jan. 28, 2011  (KR) .................. 10-2011-0008802
Mar. 30, 2011  (KR) .................. 10-2011-0029045

(51) Int. Cl.
*A61B 6/04* (2006.01)
*A61B 6/00* (2006.01)
*A61B 6/03* (2006.01)
*G03B 17/56* (2006.01)
*G03B 42/02* (2006.01)

(52) U.S. Cl.
CPC . *A61B 6/56* (2013.01); *A61B 6/035* (2013.01); *A61B 6/0421* (2013.01); *A61B 6/42* (2013.01); *A61B 6/502* (2013.01); *G03B 17/561* (2013.01); *G03B 42/021* (2013.01); *G03B 2205/0053* (2013.01)

(58) Field of Classification Search
CPC .... A61B 6/502; A61B 6/0414; A61B 6/4441; A61B 6/4452; A61B 6/4417; A61B 6/4435; A61B 6/4458; A61B 6/035; H05G 1/02
USPC ................... 378/37, 193, 195, 196
See application file for complete search history.

(56) References Cited

U.S. PATENT DOCUMENTS

| 4,082,955 A * | 4/1978 | Sell ............................. 378/26 |
| 6,999,554 B2 | 2/2006 | Mertelmeier |
| 2010/0128840 A1 | 5/2010 | Cha |

FOREIGN PATENT DOCUMENTS

| JP | 2007-151603 A | 6/2007 |
| KR | 10-2007-0004190 A | 1/2007 |
| KR | 10-2008-0104722 A | 12/2008 |
| KR | 10-2010-0055975 A | 5/2010 |

* cited by examiner

Primary Examiner — Jurie Yun
(74) Attorney, Agent, or Firm — IP Legal Services, LLC

(57) ABSTRACT

The present invention relates to a photographing device including a power transmission unit. The power transmission unit includes a frame unit which is connected to the second drive body, an adaptor unit which is connected to the frame unit and is selectively connected to the first drive body or the support body by external power, an actuating unit which operates the adaptor unit, and a power unit which transmits power to the actuating unit. According to the power transmission unit of the X-ray mammography device, since biopsy photography and tomography can be performed using only one power transmission unit, the weight and size of the rotating arm may be reduced, and the vibration and noise produced thereby may be reduced. Thanks to the simple operation mechanism of the power transmission unit, power loss may be reduced, and the durability of each component may be improved.

25 Claims, 8 Drawing Sheets

PHOTOGRAPHING DEVICE INCLUDING A POWER TRANSMISSION BODY SELECTIVELY COUPLED TO A ROTATING ARM AND TO A SUPPORT

CROSS REFERENCE TO RELATED APPLICATIONS

This application is a National Stage Patent Application of PCT International Patent Application No. PCT/KR2011/002248 (filed on Mar. 31, 2011) under 35 U.S.C. §371, which claims priority to Korean Patent Application Nos. 10-2011-0008802 (filed on Jan. 28, 2011) and 10-2011-0029045 (filed on Mar. 30, 2011), the teachings of which are incorporated herein in their entireties by reference.

TECHNICAL FIELD

The present invention relates, in general, to photographing devices and, more particularly, to a photographing device which includes a power transmission unit that is selectively connected to a rotating arm or a support body.

BACKGROUND ART

Generally, an X-ray mammography device, which is one example of photographing device, is a device used to perform the early diagnosis of a tumor which may occur in the breast of a patient. The X-ray mammography device transmits an appropriate quantity of X-rays through the breast of the patient and senses the transmitted X-rays to obtain an image.

In such an X-ray mammography device, the breast of the patient is located between an X-ray source and an X-ray receiving unit. Thereafter, the breast is fixed by a separate pressing plate, and X-rays are applied to the breast that is in the pressed state.

A representative example of an X-ray mammography device according to a conventional technique was proposed in U.S. Pat. No. 6,999,554 B2. FIG. 1 illustrates an X-ray mammography device introduced in this technique.

As shown in the drawing, a support arm 3 is provided on an upper end of a support body 1 which functions as a basic support. A rotating arm 5 which rotates around a longitudinal axis of the support arm 3 is connected to the support arm 3.

An X-ray source 7 which emits X-rays is provided on a front end of the rotating arm 5. An X-ray receiving unit 9 is provided on a front end of the support arm 3 and is oriented facing the X-ray source 7.

Furthermore, a pressing plate 11 is provided on the support arm 3 between the X-ray source 7 and the X-ray receiving unit 9 so as to hold a breast B of a patient.

The support arm 3 is rotated by a first electric motor 13, and the rotating arm 5 is rotated by a second electric motor 15. The X-ray receiving unit 9 is rotated by a third electric motor 17.

The X-ray mammography device having the above-mentioned construction is configured such that not only typical mammography but also biopsy photography or tomography can be performed. Typically, in a mammography mode, after the breast of a patient has been held by the pressing plate 11, the X-ray receiving unit 9 and the X-ray source 7 rotate around the breast to photograph it while the relative positions between the X-ray receiving unit 9 and the X-ray source 7 are fixed.

In the biopsy photography or tomography mode, while the pressing plate 11 and the X-ray receiving unit 9 are fixed in the position, only the X-ray source 7 is rotated to create two-dimensional images taken from a variety of angles.

However, the X-ray mammography device requires three electric motors to respectively operate the support arm 3, the rotating arm 5 and the X-ray receiving unit 9. Furthermore, separate connectors for connecting the respective electric motors to the associated components are also required.

In other words, the conventional X-ray mammography device must have both the photographing mode in which the X-ray receiving unit 9 and the X-ray source 7 are rotated in a state of being fixed with respect to each other, and the photographing mode in which the X-ray receiving unit 9 and the X-ray source 7 are independently rotated relative to each other. Therefore, at least two electric motors are required.

The additional electric motor and associated connectors increase a load applied to the support arm 3 and the rotating arm 5. As a result, there is a problem in that the size of the entire device is increased.

Furthermore, a separate mechanism and control system are required to control the electric motors and the connectors, thus increasing the production cost.

In addition, an increase in the weight of the components increases the capacity of each motor. This increases vibrations and noise and reduces the durability of the components.

DISCLOSURE

Technical Problem

Accordingly, the present invention has been made keeping in mind the above problems occurring in the prior art, and an object of the present invention is to provide a photographing device which includes a power transmission unit that is configured such that rotation that is selectively dependent on a rotary body can be embodied.

Technical Solution

In order to accomplish the above object, in an aspect, the present invention provides A photographing device, including: a power source; a support body; a first drive body connected to the support body so as to be rotatable, the first drive body being rotated by power of the power source; a second drive body selectively connected to the first drive body so as to be rotatable; a power transmission unit selectively connecting the second drive body to the first drive body or the support body; a light source provided on one of the first drive body and the second drive body; and a light receiving unit provided on a remaining one of the first drive body or the second drive body.

In another aspect, the present invention provides a photographing device, including: a support body provided with a power source; a first drive body provided with a light source for photographing and connected to the support body so as to be rotatable, the first drive body being rotated by power of the power source; a second drive body receiving light emitted from the light source of the first drive body, the second drive body being selectively connected to the first drive body so as to be rotatable; and a power transmission unit connected to the second drive body, the power transmission unit selectively connecting the second drive body to the first drive body or the support body.

The photographing device may further include: a first connection unit provided between the support body and the first drive body, the first connection unit rotatably connecting the first drive body to the support body; and a second connection unit provided between the first drive body and the second drive body, the second connection unit rotatably connecting the second drive body to the first drive body.

The first connection unit may rotate the first drive body depending on rotation of the power source, and the second connection unit may rotate the second drive body using power transmitted by the power transmission unit.

The power transmission unit may connect the first drive body to the second drive body so that the first drive body and the second drive body are integrally rotated by rotation of the power source, or the power transmission unit may connect the second drive body to the support body so that only the first drive body is rotated.

The power transmission unit may include an adaptor unit provided to be moved towards the first drive body or the support body by a power unit provided in the power transmission unit and to be selectively connected to the first drive body or the support body.

The adaptor unit may include: a first adaptor inserted into a connection depression of the first drive body; and a second adaptor inserted into a connection depression of the support body.

The power transmission unit may include: a frame unit connected to the second drive body; an adaptor unit connected to the frame unit, the adaptor unit being selectively connected to the first drive body or the support body by external power; and an actuating unit provided in the frame unit, the actuating unit operating the adaptor unit.

The photographing device may further include a power unit providing power to the actuating unit.

The adaptor unit may include: a plate connected to the actuating unit; a first adaptor provided on a first surface of the plate, the first adaptor being selectively connected to the first drive body; and a second adaptor provided on a second surface of the plate, the second adaptor being selectively connected to the support body.

The first adaptor may have a cylindrical protrusion shape and be seated into a connection depression formed in the first drive body.

The second adaptor may be a cylindrical protrusion shape and be seated into a connection depression formed in the support body.

The actuating unit may include: a ball screw provided in the frame unit and connected at an end thereof to the power unit; and a spline threadedly coupled to the ball screw and connected at an end thereof to the adaptor unit.

The frame unit may include: a first bracket connected to the second drive body; a second bracket connected to the first bracket; and a plurality of connection rods connecting the first bracket to the second bracket.

The adaptor unit may include a guide unit assisting and guiding movement of the adaptor unit.

The guide unit may include: a ball shaft connected to the adaptor unit; and a housing connected to the ball shaft.

The first adaptor may include a magnet unit generating magnetic force along with the connection depression or an elastic member providing elastic force to the protrusion-shaped first adaptor.

The second adaptor may include a magnet unit generating magnetic force along with the connection depression or an elastic member providing elastic force to the protrusion-shaped first adaptor.

The power transmission unit may be configured such that the first drive body and the second drive body are manually connected to each other or manually disconnected from each other, and the second drive body and the support body are manually connected to each other or manually disconnected from each other.

The power transmission unit may include: a frame unit connected to the second drive body; a movable adaptor connected to the frame unit, the movable adaptor being manually connected to the first drive body or the support body; and a conversion unit provided on the movable adaptor, the conversion unit manually converting a connection state of the movable adaptor.

The movable adaptor may be provided in a plate of the frame unit and have a protrusion shape that is selectively protruded towards the first drive body or the support body and is inserted into a connection depression of the first drive body or a connection depression of the support body.

The movable adaptor may include: a protrusion part sliding along a guide channel formed in the plate; and a removal prevention part preventing the protrusion part from being removed from the plate.

The conversion unit may include: a rotary core provided in the frame unit; a handle connected to the rotary core; and a rotary block connected to the rotary core, the rotary block coming into contact with a support block provided on the movable adaptor.

The photographing device may comprise an X-ray mammography device. When in a mammography mode, the first drive body and the second drive body may be connected to each other so that the first and second drive bodies are integrally rotated. When in a biopsy photography or tomography mode, the first drive body and the second drive body may be disconnected from each other, and the second drive body and the support body may be connected to each other.

The X-ray mammography device may further include a pressing unit configured to press a breast of a patient.

Advantageous Effects

A power transmission unit of a photographing device according to the present invention can reduce the weight and size of a rotating arm and also reduce vibration and noise produced thereby. Furthermore, a light receiving unit is operated via a simple operating mechanism using rotating force of the rotating arm. Therefore, power loss may be reduced, and the durability of each component may be improved.

BEST MODE

Hereinafter, a preferred embodiment of the present invention will be described in detail with reference to the attached drawings. Although, in the following description, an X-ray mammography device will be introduced as an example of a photographing device according to the present invention, light of a light source for providing an image is not limited to an X-ray, and use of the photographing device is also not limited to mammography. Depending on the kind of the photographing device, an X-ray source unit which will be described herein below may comprise a light source or a signal transmitter, and an X-ray receiving unit may comprise a light receiver or a signal receiver.

FIGS. 2 through 13 illustrate a preferred embodiment of a power transmission unit of an X-ray photographing device as an example of a photographing device according to the present invention.

Figure 1:
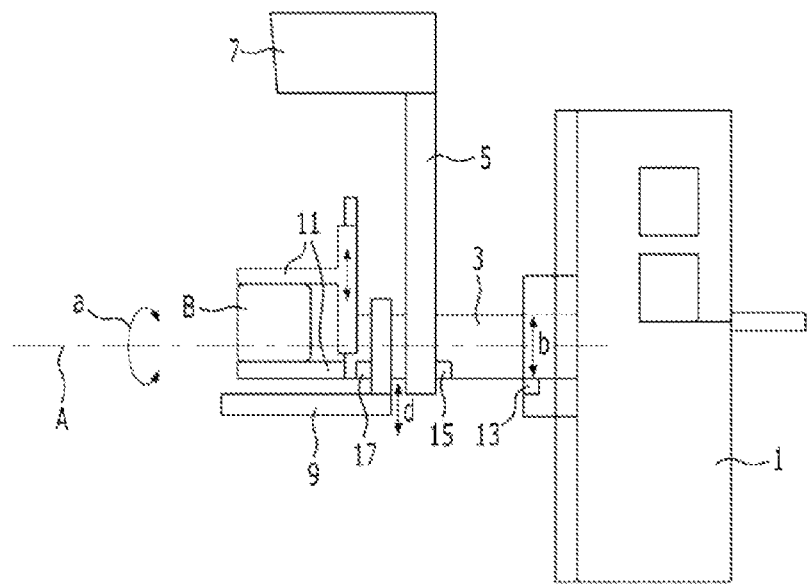
FIG. 1 is a front view showing an X-ray mammography device which is an embodiment of a conventional photographing device.
Figure 2:
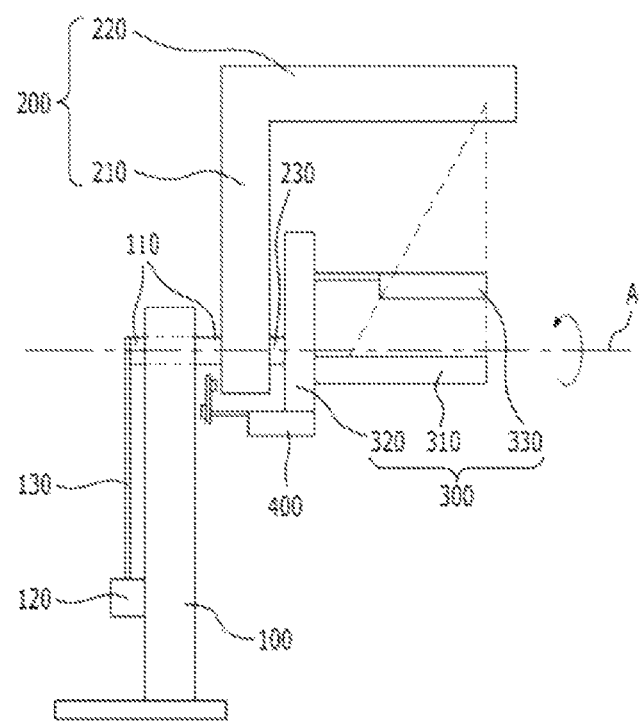
FIG. 2 is a front view illustrating the construction of an X-ray mammography device having a power transmission unit, according to an embodiment of the present invention.
Figure 3:
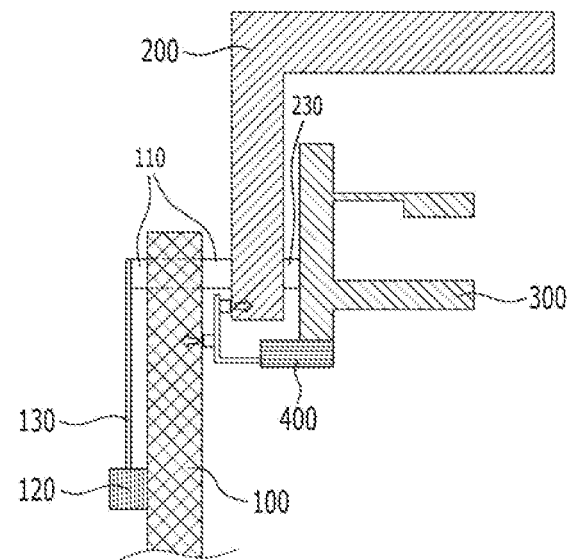
FIG. 3 is a schematic view showing the construction of the power transmission unit and a connection relationship among the power transmission unit, an X-ray sensing unit, a rotating arm and a support body according to the embodiment of the present invention.

Referring to FIGS. 2 and 3, the X-ray photographing device according to the present invention includes a support body 100, which is a stand of the photographing device of the present invention; a first drive body 200, which is rotatably connected to the support body 100; a second drive body 300, which is rotatably connected to the first drive body 200; and a power transmission unit 400, which is configured such that rotation of the second drive body 300 is selectively dependent on rotation of the first drive body 200.

The support body 100 functions to support the photographing device according to the present invention. The first drive body 200 is connected to the support body 100 on an upper end of the support body 100 by a first connection unit 110. The first connection unit 110 is a general actuation assembly which is provided to rotate the first drive body 200. The first connection unit 110 may include different kinds of gear assemblies, a gear drum, a gear shaft, a ball bearing, etc.

Furthermore, a power source 120 is provided on the support body 100 to supply power to the first drive body 200. Power generated by the power source 120 is transmitted to the first connection unit 110. The first connection unit 110 is disposed in a hole formed through the upper end of the support body 100. A first end of the first connection unit 110 is connected to the first drive body 200, and a second end thereof is connected to the power source 120.

The power source 120 may be configured such that it is directly connected to the first connection unit 110 or is indirectly connected thereto. As shown in FIG. 2, in the case where the first connection unit 110 is directly connected to the power source 120, power can be transmitted from the power source 120 to the first connection unit 110 by a connector 130 such as a connection chain.

The first drive body 200 is rotatably connected to the support body 100 and emits light such as X-rays. The first drive body 200 includes a rotating arm 210 which rotates around axis A. An X-ray source 220 which emits X-rays integrally extends from an end of the rotating arm 210 in a direction perpendicular to the longitudinal direction of the rotating arm 210.

The second drive body 300 is rotatably connected to the first drive body 200 by a second connection unit 230. The second drive body 300 receives light emitted from the first drive body 200.

The second connection unit 230 includes a general actuation assembly which is used to rotate the second drive body 300, in the same manner as that of the first connection unit 110.

Furthermore, the second connection unit 230 is not dependent on the first connection unit 110. Therefore, the second connection unit 230 is independently operated without being interlocked with the rotation of the first connection unit 110. In other words, the second drive body 300 is selectively connected to and rotated subject to the first drive body 200 by the power transmission unit 400 rather than being rotated by interlock between the first connection unit 110 and the second connection unit 230.

The second drive body 300 includes an X-ray receiving unit 310 which is disposed facing the X-ray source 220 to receive an X-ray emitted from the X-ray source 220. The X-ray receiving unit 310 is removably connected to the support unit 320. The support unit 320 is rotatably connected to an end of the rotating arm 210 by the second connection unit 230.

In the case where the photographing device according to the present invention is used to embody mammography, the second drive body 300 may further include a pressing unit 330 which holds the human breast.

The power transmission unit 400 according to a first embodiment of the present invention is connected to the second drive body 300. In detail, the power transmission unit 400 is preferably connected to the support unit 320 of the second drive body 300. The power transmission unit 400 is configured such that rotation of the second drive body 300 is selectively dependent on rotation of the first drive body 200. Various clutches or transmitters can be used to embody the power transmission unit 400.

FIG. 3 schematically illustrates the construction of the photographing device which is operated by the power transmission unit 400 of the present invention. As shown in FIG. 3, the first drive body 200 is rotated by the power source 120 of the support body 100. The rotation of the second drive body 300 is selectively dependent on the rotation of the first drive body 200 depending on the operation of the power transmission unit 400.

Figure 4:
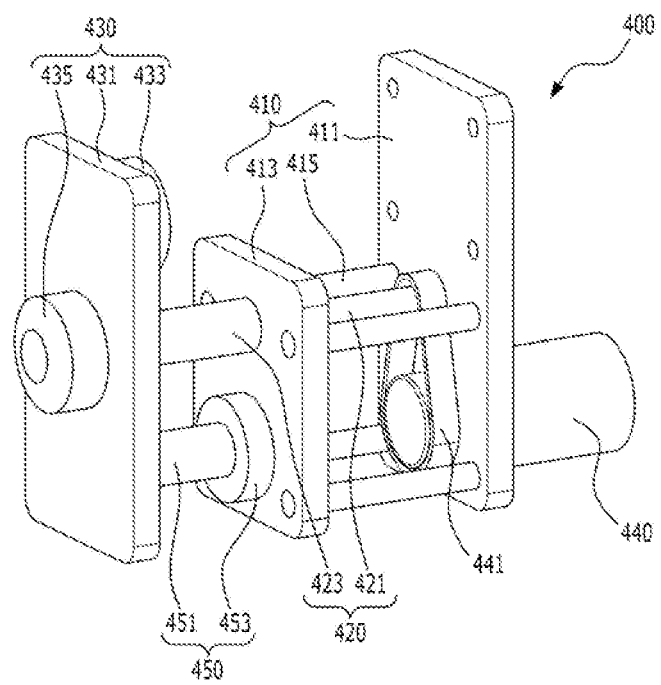
FIG. 4 is a perspective view illustrating a preferred example of the construction of the power transmission unit of the X-ray mammography device according to the embodiment of the present invention.
Figure 5:
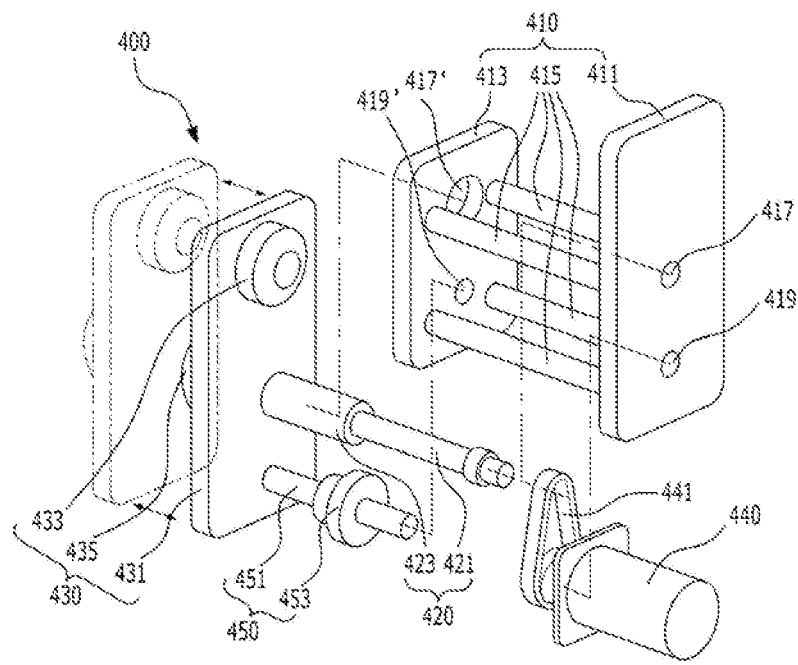
FIG. 5 is an exploded perspective view of FIG. 4.

FIGS. 4 and 5 schematically illustrate the construction of the power transmission unit 400 according to the first embodiment of the present invention. As shown in the drawings, the power transmission unit 400 includes a frame unit 410, which functions as a basic support; an adaptor unit 430, which is selectively connected to the rotating arm 210 or the support body (stand) 100 by external power to control the direction of power transmission; and an actuating unit 420, which is connected to the frame unit 410 and moves the adaptor unit 430.

The actuating unit 420 is connected to a power unit 440. The power unit 440 is a small power source which is provided to operate components of the power transmission unit 400 of the present invention. The power unit 440 is a different kind of power source from the large capacity power source 120 that is provided in the photographing device As shown in FIG. 4, the frame unit 410 includes a first bracket 411 and a second bracket 413, which are provided facing each other.

The first bracket 411 is fixed to the support unit 320. The second bracket 413 is connected to only the first bracket 411 by a plurality of connection rods 415 without being connected to the support unit 320.

The actuating unit 420 includes a ball screw 421, and a spline 423 which is threadedly coupled to the ball screw 421 so as to be movable in the longitudinal direction of the ball screw 421.

A plurality of connection holes 417, 417', 419 and 419' are formed in the first and second brackets 411 and 413. Among the connection holes, the actuating unit 420 that is provided to move the adaptor unit 430 is disposed in the first connection holes 417 and 417', which are formed in upper portions of the first and second brackets 411 and 413. The power unit 440 is connected to the second connection hole 419, which is formed in a lower portion of the first bracket 411. A guide unit 450 is connected to the second connection hole 419', which is formed in a lower portion of the second bracket 413.

The ball screw 421 of the actuating unit 420 functions to move the adaptor unit 430 and is configured such that the distance that the spline 423 moves forwards or rearwards can be adjusted. The spline 423 functions to prevent a plate 431 provided with adaptors 433 and 435 on opposite sides thereof from being rotated to the left or the right and thus reduce the degree of freedom.

Although the actuating unit 420 has been illustrated as including the ball screw 421 and the spline 423, the construction of the actuating unit 420 is not limited to this, and it can be embodied by a variety of ways, for example, using an LM guide, a linear motor, etc.

A first end of the ball screw 421 is connected to the power unit 440. When the ball screw 421 is rotated by the power unit 440, the spline 423 can move along the longitudinal direction of the ball screw 421. In addition, the distance that the spline 423 moves can be adjusted by controlling the number of revolutions of the power unit 440.

The adaptor unit 430 is connected to the spline 423. Therefore, as the spline 423 moves, the adaptor unit 430 can also move.

As the ball screw 421 is rotated by the power unit 440, the spline 423 is moved. As the spline 423 is moved, the adaptor unit 430 can be selectively connected to the first drive body 200 or the support body 100.

The adaptor unit 430 includes the plate 431, which is connected to the spline 423 in such a way that a first surface thereof faces the first drive body 200 while a second surface thereof faces the support body 100, the first adaptor 433, which is provided on the first surface of the plate 431, and the second adaptor 435, which is provided on the second surface of the plate 431.

Referring to FIG. 5, the plate 431 can be moved towards the first drive body 200 or the support body 100 by the actuating unit 420. Thereby, the first adaptor 433 is connected to the first drive body 200, or the second adaptor 435 is connected to the support body 100.

Each of the first and second adaptor 433 and 435 can have a variety of shapes. One embodiment of the shapes of the first and second adaptor 433 and 435 is a protrusion shape.

Figure 6:
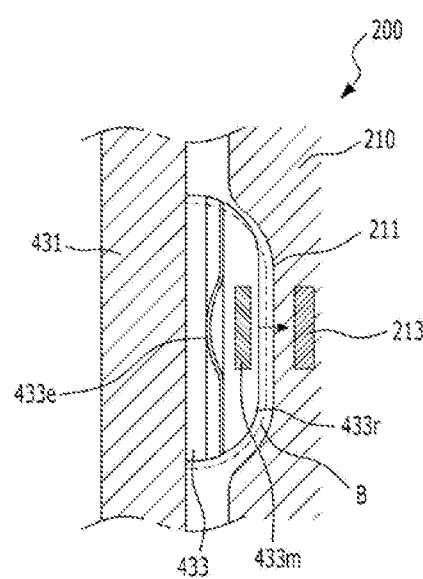
FIG. 6 is a sectional view showing a first adaptor of the power transmission unit of the X-ray mammography device according to the embodiment of the present invention.

As shown in FIG. 6, the first adaptor 433 has a cylindrical protrusion shape. The cylindrical protrusion is inserted into or removed from a connection depression 211 formed in the rotating arm 210 of the first drive body 200, whereby the first adaptor 433 can be selectively connected to the first drive body 200.

A rounded surface part 433r having a predetermined curvature is formed on a corner of a front end of the cylindrical protrusion which forms the first adaptor 433. The rounded surface part 433r functions to make the first adaptor 433 having a cylindrical protrusion shape to be smoothly inserted into the connection depression 211 even when the first adaptor 433 is slightly misaligned from the connection depression 211 because of vibrations or the tolerance of the power transmission unit itself.

Even if the first adaptor 433 is not correctly aligned with the connection depression 211, in other words, as shown in FIG. 6, even if the first adaptor 433 is not disposed at a position at which it is accurately inserted into the connection depression 211, the edge of a mouth of the connection depression 211 is brought into contact with the rounded surface part 433r, so that the first adaptor 433 slides towards position B designated by the dotted line of FIG. 6. Thereby, the first adaptor 433 can be smoothly inserted into the connection depression 211.

Furthermore, to make insertion of the first adaptor 433 into the connection depression 211 more reliable, a magnet 433m may be provided in the first adaptor 433. Even if a predetermined extent of misalignment occurs, the first adaptor 433 can be smoothly inserted into the connection depression 211 by attractive force between the magnet 433m provided in the first adaptor 433 and a magnet 213 provided in a central portion of the connection depression 211.

Further, a separate elastic member 433e may be provided in the first adaptor 433. The elastic member 433e can be embodied by a plate spring so that, when external force is applied to the first adaptor 433, the first adaptor 433 can be elastically compressed. The elastic member 433e can function to absorb shock generated when the first adaptor 433 is inserted into the connection depression 211.

Therefore, even if the first adaptor 433 is not precisely aligned with the connection depression 211, because the first adaptor 433 can be elastically compressed by the elastic member 433e, the first adaptor 433 can be smoothly inserted into the connection depression 211.

In addition, the first adaptor 433 may be formed of flexible plastic or stainless steel so that the first adaptor 433 can be elastically compressed by itself.

The second adaptor 435 has the same shape as that of the first adaptor 433. A connection depression 103 into which the second adaptor 435 can be inserted is formed in the support body 100 in the same shape as that of the connection depression 211 formed in the rotating arm 210. A magnet is provided in the support body 100 at a position facing a magnet which is provided in the second adaptor 435.

Each of the first and second adaptors 433 and 435 may have a polygonal protrusion shape as well as a cylindrical protrusion shape.

Referring again to FIG. 4, the power unit 440 is formed of a rotary motor or the like which is connected to an end of the ball screw 421. The power unit 440 may be directly connected to the ball screw 421. Alternatively, as shown in FIG. 4, the power unit 440 may be indirectly connected to the ball screw 421 by a timing belt 441.

The guide unit 450 is connected to the plate 431 of the adaptor unit 430. The guide unit 450 functions to guide the direction of movement of the adaptor unit 430. For this, the guide unit 450 includes at least one fixed member 451 which supports the adaptor unit 430 and is connected to the plate 431.

The fixed member 451 passes through a central portion of the ball shaft 453 so that the ball shaft 453 can move horizontally in the direction in which the adaptor unit 430 moves. The ball shaft 453 includes a separate bearing (not shown) to make the movement of the ball shaft 453 smoother. A first side of the ball shaft 453 makes contact with the second bracket 413 while a second side thereof does not.

Figure 7:
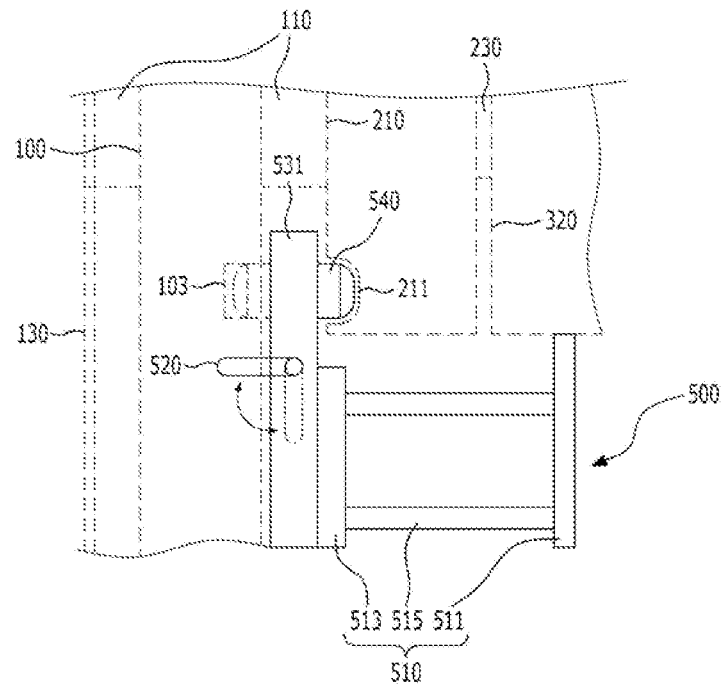
FIG. 7 is a front view illustrating a power transmission unit of an X-ray mammography device, according to another embodiment of the present invention.
Figure 8:
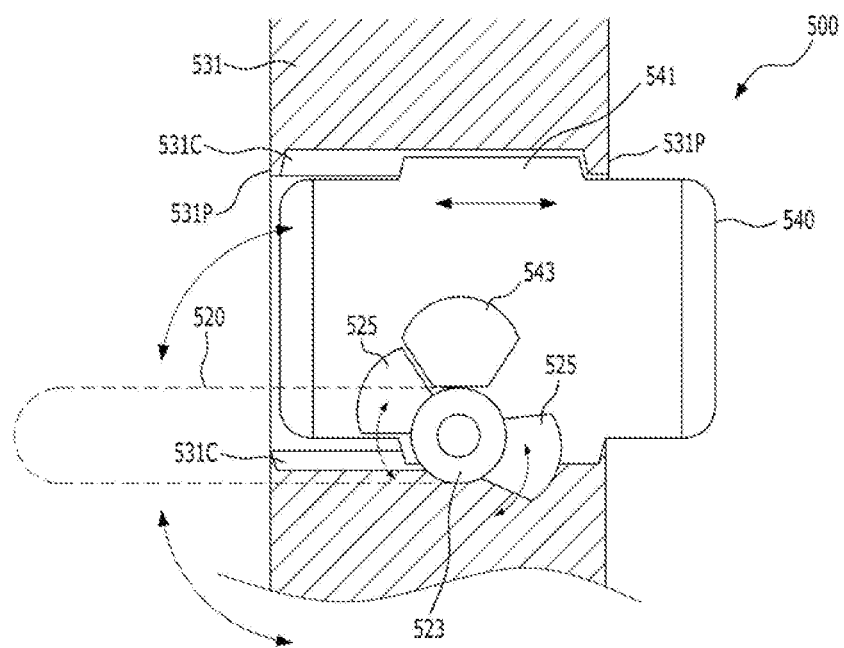
FIG. 8 is a sectional view showing the construction of the power transmission unit of FIG. 7.

FIGS. 7 and 8 illustrate a power transmission unit 500 which is manually operated, according to a second embodiment of the present invention.

As shown in FIG. 7, the power transmission unit 500 according to the second embodiment of the present invention includes a first bracket 511, which is connected to the support unit 320 of the second drive body 300, and a frame unit 510, which has a plurality of connection rods 515 that connect the first bracket 511 to the second bracket 513.

The plate 531 is connected to a surface of the second bracket 513. A movable adaptor 540 which is moved towards the first drive body 200 or the support body 100 by a conversion unit 520 is provided in the plate 531.

The movable adaptor 540 is a component, such as a protrusion described above, which is inserted into the connection depression 211 of the first drive body 200 or the connection depression 103 of the support body 100. The movable adaptor 540 is disposed in a hole formed through the movable adaptor 540.

As shown in FIG. 8, the movable adaptor 540 has a cylindrical shape. A protrusion part 541 which has a diameter larger than that of the movable adaptor 540 and protrudes outwards from the surface of the movable adaptor 540 is provided around a circumferential outer surface of the cylindrical movable adaptor 540.

The protrusion part 541 of the movable adaptor 540 is slidably disposed in a guide channel 531c formed in the plate 531. Removal prevention parts 531p are provided on respective opposite ends of the guide channel 531c of the plate 531 so as to prevent the protrusion part 541 from being removed from the guide channel 531c. Therefore, the movable adaptor 540 can slide along the guide channel 531c of the plate 531, but it is blocked by the removal prevention parts 531p so that the movable adaptor 540 can be prevented from being undesirably removed from the guide channel 531c.

The conversion unit 520 which functions to move the movable adaptor 540 is provided on the plate 531. The conversion unit 520 moves the movable adaptor 540 by operating a handle 521, so that the movable adaptor 540 is selectively inserted into the connection depression 211 of the first drive body or the connection depression 103 of the support body 100.

The conversion unit 520 includes the handle 521, which is held and turned by a user, a rotary core 523, which is provided on an end of the handle 521, and a rotary block 525, which protrudes outwards from the rotary core 523.

The rotary block 525 includes two arc-shaped blocks which are spaced apart from each other by a predetermined distance. The rotary block 525 is configured such that it selectively comes into contact with a support block 543. Therefore, when the user holds the handle 521 and rotates it, the rotary block 525 is rotated by the rotation of the handle 521. Then, the support block 543 which is disposed at a side of the rotary blocks 525 is brought into contact with the rotary block 525 and is moved by it, whereby the movable adaptor 540 is moved in one direction.

The power transmission unit, described above, which is manually operated, is not limited to the explanation of this specification. In other words, the power transmission unit can have any type structure, so long as the protrusion-shaped movable adaptor 540 can be selectively connected to the rotating arm 210 of the first drive body 200 or the support body 100 manually.

Moreover, the shape of the adaptor of the power transmission unit that is automatically or manually operated is not limited to a protrusion shape. The adaptor can be embodied in a variety of shapes as long as it can selectively control the connection between the power transmission unit and the first drive body or the support body. Furthermore, the shape of each of the connection depressions that are formed in the rotating arm of the first drive body and the support body is determined depending on the shape of the adaptor.

The X-ray photographing device including the power transmission unit according to the present invention further includes a control unit (not shown) which controls the operation of the X-ray photographing device or the power transmission unit. Furthermore, the X-ray photographing device may further include an angle measurement sensor (not shown) which measures an angle at which the rotating arm 210 or the X-ray receiving unit 310 is rotated. A zero-adjustment state of the X-ray receiving unit 310 can be checked by the angle measurement sensor.

Hereinafter, the operation of the power transmission unit of the photographing device according to the present invention having the above-mentioned construction will be described in detail.

The X-ray mammography device according to the present invention is configured such that it can carry out mammography, biopsy photography for obtaining tomography information about tissues of a target to be examined, or tomography for making three-dimensional images about the target.

Typically, the mammography is performed in such a way that the X-ray source 220 provided on the first drive body 200 and the X-ray receiving unit 310 provided on the second drive body 300 are integrally rotated in the vertical direction. Another embodiment in which the X-ray receiving unit is provided on the first drive body 200 and the X-ray source is provided on the second drive body 300 also falls within the bounds of the present invention. Further, the biopsy photography or tomography is conducted in such a way that only the X-ray source 220 of the first drive body 200 is rotated while the X-ray receiving unit 310 provided on the second drive body 300 is connected to the support body 100.

Figure 9:
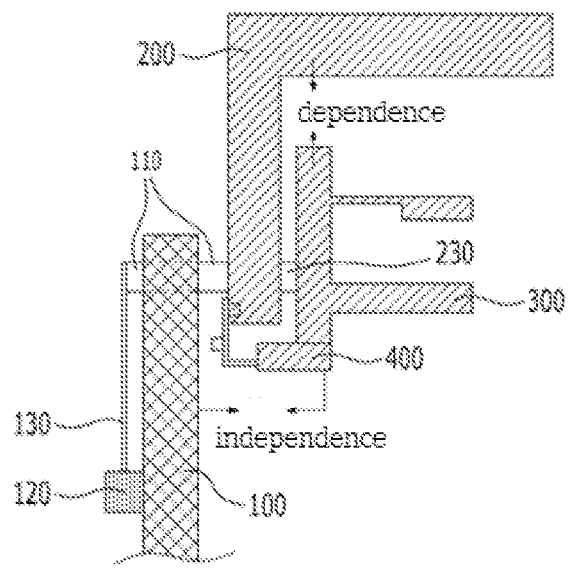
FIGS. 9 and 10 are views illustrating the assembly structure of components of the X-ray mammography device according to the present invention
Figure 10:
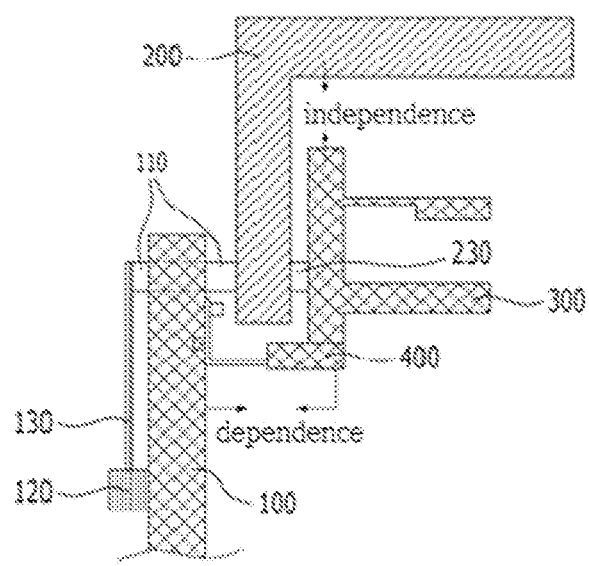

With regard to this, FIGS. 9 and 10 schematically illustrate the operation of the device. FIG. 9 illustrates the operation of the device when in the mammography mode. In this case, the power transmission unit 400 of the present invention connects the first drive body 200 to the second drive body 300 so that the first drive body 200 and the second drive body 300 can be integrally rotated by the power source 120.

FIG. 10 illustrates the operation of the device when in the biopsy photography or tomography mode. In this case, the power transmission unit 400 of the present invention connects the second drive body 300 to the support body 100 so that only the first drive body 200 is rotated while the second drive body 300 is fixed to the support body 100.

Figure 11:
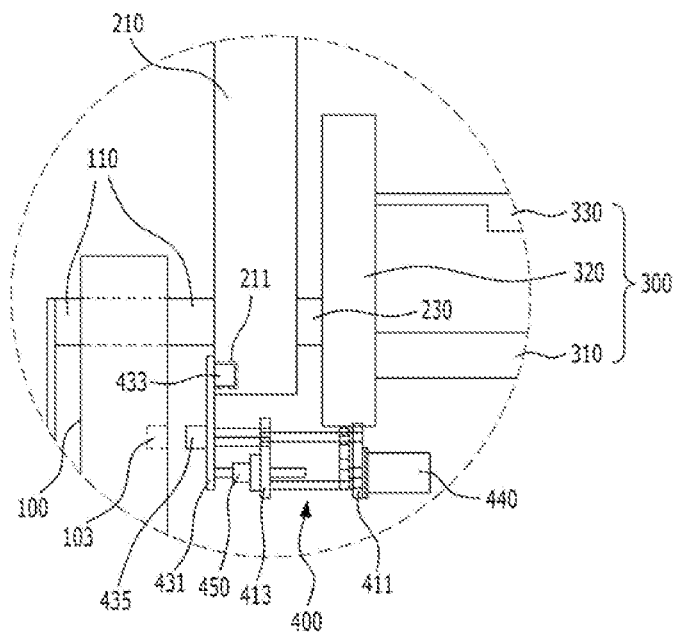
FIGS. 11 through 13 are views showing the operation of the power transmission unit of the X-ray mammography device according to the present invention.
Figure 12:
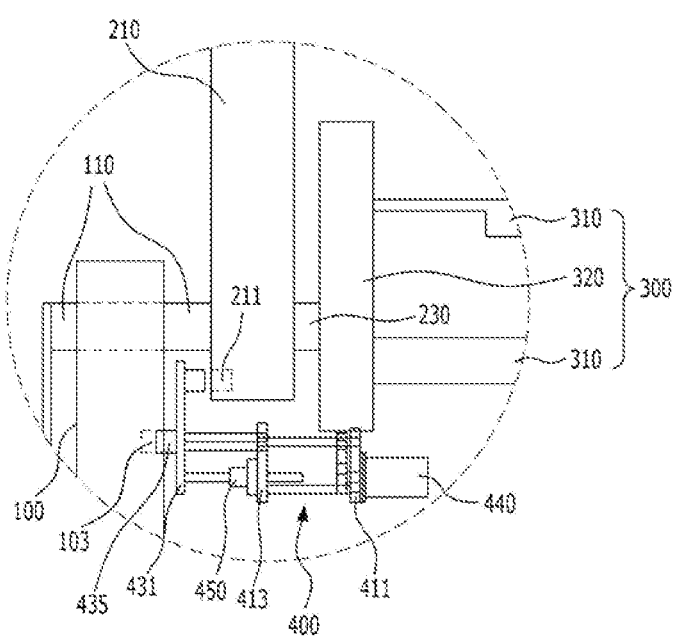
Figure 13:
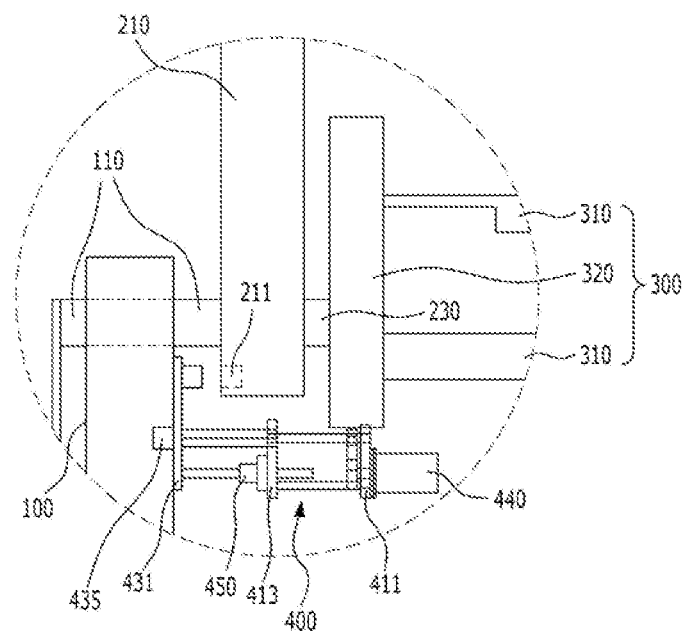
Figure 14:
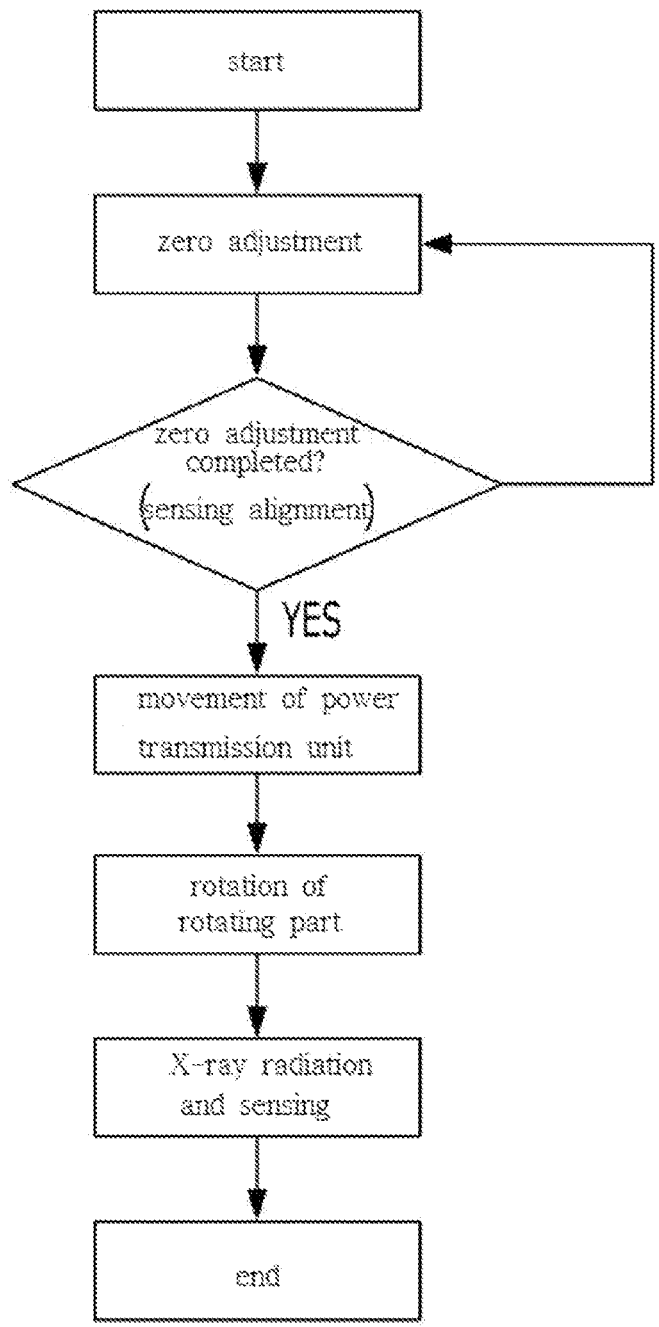
FIG. 14 is a flowchart showing a method of controlling the X-ray mammography device according to the present invention.

FIGS. 11 through 13 illustrate in more detail the conditions of the device when in the respective photographing modes.

As shown in FIG. 11, in the mammography mode, the first adaptor 433 of the power transmission unit 400 is inserted into the connection depression 211 of the rotating arm 210 of the first drive body 200. The second adaptor 435 is removed from the connection depression 103 of the support body 100. In this way, the power transmission unit 400 integrally connects the rotating arm 210 of the first drive body 200 to the X-ray receiving unit 310 of the second drive body 300. Thereby, the rotating arm 210 and the X-ray receiving unit 310 are integrally rotated.

Meanwhile, in the biopsy photography or tomography mode, zero adjustment of the rotating arm 210 or the X-ray receiving unit 310 is carried out such that the rotating arm 210 or the X-ray receiving unit 310 is set to the zero point that is the reference point.

After the zero adjustment has been completed, the angle measurement sensor checks whether the rotating arm 210 or the X-ray receiving unit 310 has been set to the zero point. If the rotating arm 210 or the X-ray receiving unit 310 is not aligned with the zero point, the zero adjustment process is conducted again by rotating the rotating arm 210.

After the zero adjusted state has been determined by the angle measurement sensor, the power transmission unit 400 is operated, whereby the X-ray receiving unit 310 of the second drive body 300 is connected to the support body 100.

As shown in FIGS. 11 through 13, when the power unit 440 of the power transmission unit 400 is rotated, the ball screw 421 is rotated. Then, the spline 423 and the adaptor unit 430 are moved towards the support body 100. Thereby, the first adaptor 433 is removed from the connection depression 211 of the rotating arm 210 of the first drive body 200, and the second adaptor 435 is inserted into the connection depression 103 of the support body 100.

When the second adaptor 435 is inserted into the connection depression 103, the magnetic force of the magnet 433m, the elastic force of the elastic member 433e and the elasticity of the second adaptor 435 itself can make the insertion of the second adaptor 435 into the connection depression 103 of the support body 100 smoother.

As such, the X-ray receiving unit 310 of the second drive body 300 is connected to the support body 100 by the operation of the power transmission unit 400 so that the X-ray receiving unit 310 is not subject to the rotation of the rotating arm 210 of the first drive body 200. In this state, while the rotating arm 210 is rotated, X-ray tomography of the human breast with respect to a predetermined direction can be conducted.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A photographing device, comprising:
   a power source;
   a support body;
   a first drive body connected to the support body so as to be rotatable, the first drive body being rotated by power of the power source;
   a second drive body selectively connected to the first drive body so as to be rotatable;
   a power transmission unit selectively connecting the second drive body to the first drive body or the support body;
   a light source provided on one of the first drive body and the second drive body; and
   a light receiving unit provided on a remaining one of the first drive body or the second drive body.

2. The photographing device according to claim 1, further comprising:
   a first connection unit provided between the support body and the first drive body, the first connection unit rotatably connecting the first drive body to the support body; and
   a second connection unit provided between the first drive body and the second drive body, the second connection unit rotatably connecting the second drive body to the first drive body.

3. The photographing device according to claim 2, wherein the first connection unit rotates the first drive body depending on rotation of the power source, and the second connection unit rotates the second drive body using power transmitted by the power transmission unit.

4. The photographing device according to claim 1, wherein the power transmission unit connects the first drive body to the second drive body so that the first drive body and the second drive body are integrally rotated by rotation of the power source, or the power transmission unit connects the second drive body to the support body so that only the first drive body is rotated.

5. The photographing device according to claim 4, wherein the power transmission unit comprises
   an adaptor unit provided to be moved towards the first drive body or the support body by a power unit provided in the power transmission unit and to be selectively connected to the first drive body or the support body.

6. The photographing device according to claim 5, wherein the adaptor unit comprises:
   a first adaptor inserted into a connection depression of the first drive body; and
   a second adaptor inserted into a connection depression of the support body.

7. The photographing device according to claim 1, wherein the power transmission unit comprises:
   a frame unit connected to the second drive body;
   an adaptor unit connected to the frame unit, the adaptor unit being selectively connected to the first drive body or the support body by external power; and
   an actuating unit provided in the frame unit, the actuating unit operating the adaptor unit.

8. The photographing device according to claim 7, further comprising
   a power unit providing power to the actuating unit.

9. The photographing device according to claim 8, wherein the actuating unit comprises:
   a ball screw provided in the frame unit and connected at an end thereof to the power unit; and
   a spline threadedly coupled to the ball screw and connected at an end thereof to the adaptor unit.

10. The photographing device according to claim 7, wherein the adaptor unit comprises:
    a plate connected to the actuating unit;
    a first adaptor provided on a first surface of the plate, the first adaptor being selectively connected to the first drive body; and
    a second adaptor provided on a second surface of the plate, the second adaptor being selectively connected to the support body.

11. The photographing device according to claim 10, wherein the first adaptor has a cylindrical protrusion shape and is seated into a connection depression formed in the first drive body.

12. The photographing device according to claim 11, wherein the first adaptor comprises a magnet unit generating magnetic force along with the connection depression or an elastic member providing elastic force to the protrusion-shaped first adaptor.

13. The photographing device according to claim 10, wherein the second adaptor has a cylindrical protrusion shape and is seated into a connection depression formed in the support body.

14. The photographing device according to claim 13, wherein the second adaptor comprises a magnet unit generating magnetic force along with the connection depression or an elastic member providing elastic force to the protrusion-shaped switched adaptor.

15. The photographing device according to claim 10, wherein the frame unit comprises:
a first bracket connected to the second drive body;
a second bracket connected to the first bracket; and
a plurality of connection rods connecting the first bracket to the second bracket.

16. The photographing device according to claim 7, wherein the adaptor unit comprises
a guide unit assisting and guiding movement of the adaptor unit.

17. The photographing device according to claim 16, wherein the guide unit comprises:
a ball shaft connected to the adaptor unit; and
a housing connected to the ball shaft.

18. The photographing device according to claim 1, wherein the power transmission unit is configured such that the first drive body and the second drive body are manually connected to each other or manually disconnected from each other, and the second drive body and the support body are manually connected to each other or manually disconnected from each other.

19. The photographing device according to claim 18, wherein the power transmission unit comprises:
a frame unit connected to the second drive body;
a movable adaptor connected to the frame unit, the movable adaptor being manually connected to the first drive body or the support body; and
a conversion unit provided on the movable adaptor, the conversion unit manually converting a connection state of the movable adaptor.

20. The photographing device according to claim 19, wherein the movable adaptor is provided in a plate of the frame unit and has a protrusion shape that is selectively protruded towards the first drive body or the support body and is inserted into a connection depression of the first drive body or a connection depression of the support body.

21. The photographing device according to claim 20, wherein the movable adaptor comprises:
a protrusion part sliding along a guide channel formed in the plate; and
a removal prevention part preventing the protrusion part from being removed from the plate.

22. The photographing device according to claim 19, wherein the conversion unit comprises:
a rotary core provided in the frame unit;
a handle connected to the rotary core; and
a rotary block connected to the rotary core, the rotary block coming into contact with a support block provided on the movable adaptor.

23. The photographing device according to claim 1, comprising an X-ray mammography device,
wherein, when in a mammography mode, the first drive body and the second drive body are connected to each other so that the first and second drive bodies are integrally rotated, and
when in a biopsy photography or tomography mode, the first drive body and the second drive body are disconnected from each other, and the second drive body and the support body are connected to each other.

24. The X-ray mammography device according to claim 23, further comprising
a pressing unit configured to press a breast of a patient.

25. A photographing device, comprising:
a support body provided with a power source;
a first drive body provided with a light source for photographing and connected to the support body so as to be rotatable, the first drive body being rotated by power of the power source;
a second drive body receiving light emitted from the light source of the first drive body, the second drive body being selectively connected to the first drive body so as to be rotatable; and
a power transmission unit connected to the second drive body, the power transmission unit selectively connecting the second drive body to the first drive body or the support body.

* * * * *

UNITED STATES PATENT AND TRADEMARK OFFICE
CERTIFICATE OF CORRECTION

PATENT NO.        : 9,060,739 B2
APPLICATION NO.   : 13/982315
DATED             : June 23, 2015
INVENTOR(S)       : Jae-Hong Kim Page 1 of 1

It is certified that error appears in the above-identified patent and that said Letters Patent is hereby corrected as shown below:

IN THE CLAIMS

In claim 14, column 12, line 67, "switched" should be amended --second--.

Signed and Sealed this
Third Day of November, 2015

Michelle K. Lee
*Director of the United States Patent and Trademark Office*